(12) United States Patent
Halsey et al.

(10) Patent No.: US 7,824,877 B2
(45) Date of Patent: Nov. 2, 2010

(54) METHODS FOR DIAGNOSING AUTO-IMMUNE CHRONIC URTICARIA

(75) Inventors: John Frederick Halsey, Prairie Village, KS (US); Michelle Lee Altrich, Lenexa, KS (US)

(73) Assignee: Viracor-IBT Laboratories, Inc., Lee's Summit, MO (US)

( * ) Notice: Subject to any disclaimer, the term of this patent is extended or adjusted under 35 U.S.C. 154(b) by 440 days.

(21) Appl. No.: 11/900,084

(22) Filed: Sep. 10, 2007

(65) Prior Publication Data

US 2009/0068686 A1 Mar. 12, 2009

(51) Int. Cl.
*G01N 33/53* (2006.01)
(52) U.S. Cl. .................. 435/7.92; 435/7.1; 424/805; 424/810
(58) Field of Classification Search .................. None
See application file for complete search history.

(56) References Cited

OTHER PUBLICATIONS

Grattan, C.E., Skin Pharmacol. 1991;4 Suppl 1:64-70.*
Sabroe et al., J Allergy Clin Immunol. Oct. 1998;102(4 Pt 1):651-8.*
Platzer et al., Allergy. Sep. 2005;60(9):1152-6.*
Hide et al., N Engl J Med. Jun. 3, 1993;328(22):1599-604.*
Napoli et al., Curr Allergy Asthma Rep. Jul. 2001;1(4):329-36.*
Guesdon et al. , J Immunol Methods. Feb. 27, 1986;87(1):69-78.*
Ferrer et al., Allergy. Aug. 2003;58(8):802-7.*
Deswerdt et al., "Detection of basophil-activating IgG autoantibodies in chronic idiopathic urticaria by induction of CD63," J Allergy Clin Immunol, Sep. 2005, vol. 116, No. 3, pp. 662-667.
Fagiolo et al., "Effects of complement inactivation and IgG depletion on skin reactivity to autologous serum in chronic idiopathic urticaria," J Allergy Clin Immunol, Sep. 2000, vol. 106, No. 3, pp. 567-572.
Sabroe et al., "Chronic idiopathic urticaria with functional autoantibodies: 12 years on," British Journal of Dermatology, (2006), vol. 154, pp. 813-819.
Soundararajan et al., "Functional assessment of pathogenic IgG subclasses in chronic autoimmune uritcaria," J Allergy Clin Immunol, Apr. 2005, vol. 115, No. 4, pp. 815-821.

* cited by examiner

*Primary Examiner*—Michael Szperka
(74) *Attorney, Agent, or Firm*—Carol L. Francis; Bozicevic, Field & Francis LLP

(57) ABSTRACT

In certain embodiments, the present invention relates to methods, compositions, and kits for diagnosing autoimmune chronic urticaria. For example, in certain embodiments, such methods generally comprise detecting the presence of auto-antibodies to cell-surface IgE receptors or cell-bound IgE in a patient. Such auto-antibodies may be detected by (a) obtaining donor basophils and associated leukocytes from one or more donors, (b) challenging the donor basophils and associated leukocytes with control serum and quantifying the amount of histamine released by the donor basophils and associated leukocytes, (c) calculating a normalized baseline of histamine release, wherein the normalized baseline of histamine release represents a mean percentage of histamine released by the basophils and associated leukocytes of an individual donor plus a specified amount above such mean, (d) reacting patient serum with the donor basophils and associated leukocytes, (e) measuring the percentage of histamine released by the donor basophils and associated leukocytes in response to the patient serum, and (f) comparing the percentage of histamine released by the donor basophils and associated leukocytes in response to the patient serum to the normalized baseline of histamine release.

22 Claims, 2 Drawing Sheets

FIGURE 1

| Patient Samples | Tubes Needed | Volume (mL) of Cell Suspension (Cell Preparation + Stimulation Buffer) | Volume (mL) of Cell Preparation (BCF and RBCs) | Volume (mL) of Stimulation Buffer | Tubes of Blood |
|---|---|---|---|---|---|
| 1 | 11 | 1.05 | 0.52 | 0.52 | 0.37 |
| 2 | 12 | 1.14 | 0.57 | 0.57 | 0.41 |
| 3 | 13 | 1.24 | 0.62 | 0.62 | 0.44 |
| 4 | 14 | 1.33 | 0.67 | 0.67 | 0.48 |
| 5 | 15 | 1.43 | 0.71 | 0.71 | 0.51 |
| 6 | 16 | 1.52 | 0.76 | 0.76 | 0.54 |
| 7 | 17 | 1.62 | 0.81 | 0.81 | 0.58 |
| 8 | 18 | 1.71 | 0.86 | 0.86 | 0.61 |
| 9 | 19 | 1.81 | 0.90 | 0.90 | 0.64 |
| 10 | 20 | 1.90 | 0.95 | 0.95 | 0.68 |
| 11 | 21 | 2.00 | 1.00 | 1.00 | 0.71 |
| 12 | 22 | 2.09 | 1.05 | 1.05 | 0.75 |
| 13 | 23 | 2.19 | 1.09 | 1.09 | 0.78 |
| 14 | 24 | 2.28 | 1.14 | 1.14 | 0.81 |
| 15 | 25 | 2.38 | 1.19 | 1.19 | 0.85 |
| 16 | 26 | 2.47 | 1.24 | 1.24 | 0.88 |
| 17 | 27 | 2.57 | 1.28 | 1.28 | 0.92 |
| 18 | 28 | 2.66 | 1.33 | 1.33 | 0.95 |
| 19 | 29 | 2.76 | 1.38 | 1.38 | 0.98 |
| 20 | 30 | 2.85 | 1.43 | 1.43 | 1.02 |
| 21 | 31 | 2.95 | 1.47 | 1.47 | 1.05 |
| 22 | 32 | 3.04 | 1.52 | 1.52 | 1.09 |
| 23 | 33 | 3.14 | 1.57 | 1.57 | 1.12 |
| 24 | 34 | 3.23 | 1.62 | 1.62 | 1.15 |
| 25 | 35 | 3.33 | 1.66 | 1.66 | 1.19 |
| 26 | 36 | 3.42 | 1.71 | 1.71 | 1.22 |
| 27 | 37 | 3.52 | 1.76 | 1.76 | 1.26 |
| 28 | 38 | 3.61 | 1.81 | 1.81 | 1.29 |
| 29 | 39 | 3.71 | 1.85 | 1.85 | 1.32 |
| 30 | 40 | 3.80 | 1.90 | 1.90 | 1.36 |
| 31 | 41 | 3.90 | 1.95 | 1.95 | 1.39 |
| 32 | 42 | 3.99 | 2.00 | 2.00 | 1.43 |
| 33 | 43 | 4.09 | 2.04 | 2.04 | 1.46 |
| 34 | 44 | 4.18 | 2.09 | 2.09 | 1.49 |
| 35 | 45 | 4.28 | 2.14 | 2.14 | 1.53 |
| 36 | 46 | 4.37 | 2.19 | 2.19 | 1.56 |

FIGURE 1 (CON'T)

| Patient Samples | Tubes Needed | Volume (mL) of Cell Suspension (Cell Preparation + Stimulation Buffer) | Volume (mL) of Cell Preparation (BCF and RBCs) | Volume (mL) of Stimulation Buffer | Tubes of Blood |
|---|---|---|---|---|---|
| 37 | 47 | 4.47 | 2.23 | 2.23 | 1.59 |
| 38 | 48 | 4.56 | 2.28 | 2.28 | 1.63 |
| 39 | 49 | 4.66 | 2.33 | 2.33 | 1.66 |
| 40 | 50 | 4.75 | 2.38 | 2.38 | 1.70 |
| 41 | 51 | 4.85 | 2.42 | 2.42 | 1.73 |
| 42 | 52 | 4.94 | 2.47 | 2.47 | 1.76 |
| 43 | 53 | 5.04 | 2.52 | 2.52 | 1.80 |
| 44 | 54 | 5.13 | 2.57 | 2.57 | 1.83 |
| 45 | 55 | 5.23 | 2.61 | 2.61 | 1.87 |
| 46 | 56 | 5.32 | 2.66 | 2.66 | 1.90 |
| 47 | 57 | 5.42 | 2.71 | 2.71 | 1.93 |
| 48 | 58 | 5.51 | 2.76 | 2.76 | 1.97 |
| 49 | 59 | 5.61 | 2.80 | 2.80 | 2.00 |
| 50 | 60 | 5.70 | 2.85 | 2.85 | 2.04 |
| 51 | 61 | 5.80 | 2.90 | 2.90 | 2.07 |
| 52 | 62 | 5.89 | 2.95 | 2.95 | 2.10 |
| 53 | 63 | 5.99 | 2.99 | 2.99 | 2.14 |
| 54 | 64 | 6.08 | 3.04 | 3.04 | 2.17 |
| 55 | 65 | 6.18 | 3.09 | 3.09 | 2.21 |
| 56 | 66 | 6.27 | 3.14 | 3.14 | 2.24 |
| 57 | 67 | 6.37 | 3.18 | 3.18 | 2.27 |
| 58 | 68 | 6.46 | 3.23 | 3.23 | 2.31 |
| 59 | 69 | 6.56 | 3.28 | 3.28 | 2.34 |
| 60 | 70 | 6.65 | 3.33 | 3.33 | 2.38 |
| 61 | 71 | 6.75 | 3.37 | 3.37 | 2.41 |
| 62 | 72 | 6.84 | 3.42 | 3.42 | 2.44 |
| 63 | 73 | 6.94 | 3.47 | 3.47 | 2.48 |
| 64 | 74 | 7.03 | 3.52 | 3.52 | 2.51 |

METHODS FOR DIAGNOSING AUTO-IMMUNE CHRONIC URTICARIA

FIELD OF THE INVENTION

The present invention relates to the field of medical diagnostics. More particularly, the present invention relates to methods, compositions, and kits for diagnosing auto-immune chronic urticaria.

BACKGROUND OF THE INVENTION

Chronic urticaria (CU) is a common skin disorder affecting 0.1 to 1% of the general population. It is characterized by recurrent, transitory, pruritic erythematous wheals on a patient's skin for approximately 6 weeks or longer. The impact of CU on the quality of life is significant. It has been demonstrated that in 30-50% of these CU patients there is an auto-immune etiology with auto-antibodies against IgE, FcεRI or FcεRII (CD23). These auto-antibodies are presumed to bind to the surface of mast cells and basophils, which initiates a signal transduction cascade that results in the secretion of histamine and other mediators.

The treatment course for those with auto-immune forms of CU is often different than for acute and transient CU (or idiopathic CU). Drugs that modulate the basic immunological aspects of the disease (e.g., methotrexate, calcineurin inhibitors, etc.) may be considered if an auto-immune etiology is established, whereas such drugs may not be useful in treating other forms of CU. Accordingly, there is a need for robust, reliable, accurate, and efficient methods for diagnosing auto-immune forms of CU.

SUMMARY OF THE INVENTION

According to certain preferred embodiments of the present invention, methods for diagnosing auto-immune chronic urticaria are provided. Such methods generally comprise detecting the presence of auto-antibodies to cell-surface IgE receptors and/or cell-bound IgE in a patient. Such auto-antibodies may be detected by (a) obtaining donor basophils and associated leukocytes from one or more donors (provided that such donors do not exhibit clinical signs of CU), (b) challenging the donor basophils and associated leukocytes with control serum and quantifying the amount of histamine released by the donor basophils and associated leukocytes (the control serum being derived from a donor who does not exhibit clinical signs of CU), (c) calculating a normalized baseline of histamine release (which represents a mean percentage of histamine released by the basophils and associated leukocytes from each of the one or more individual donors plus a specified amount above such mean), (d) reacting test (patient) serum with the donor basophils and associated leukocytes, (e) measuring the percentage of histamine released by the donor basophils and associated leukocytes in response to the test (patient) serum, and (f) comparing the percentage of histamine released by the donor basophils and associated leukocytes in response to the test (patient) serum to the normalized baseline of histamine release. If the percentage of histamine released by the donor basophils and associated leukocytes in response to the test (patient) serum is sufficiently greater than the normalized baseline of histamine release, as described herein, the patient may be diagnosed with auto-immune CU.

As described in more detail below, such methods are further useful for (i) preparing donor basophils and associated leukocytes for use in diagnosing auto-immune chronic urticaria, (ii) detecting and measuring auto-antibodies to cell-surface IgE receptors or cell-bound IgE in a patient, and (iii) determining whether a patient should be treated with an immune modulating drug.

According to additional embodiments of the present invention, kits are provided which contain donor basophils and associated leukocytes for use in diagnosing auto-immune chronic urticaria. Such kits preferably include instructions and/or other information, which convey the normalized baseline of histamine release (as described below) for the applicable donor basophils and associated leukocytes.

The above-mentioned and additional features of the present invention are further illustrated in the Detailed Description contained herein.

BRIEF DESCRIPTION OF THE FIGURES

FIG. 1 is a table that lists exemplary amounts of cell suspension, stimulation buffer, and other agents that may be added to each reaction tube described in the Examples below.

DETAILED DESCRIPTION OF THE INVENTION

The following will describe in detail several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used, and made without departing from the scope and spirit of the invention.

According to certain preferred embodiments of the present invention, methods for diagnosing auto-immune chronic urticaria are provided. Such methods generally comprise detecting the presence of auto-antibodies to cell-surface IgE receptors and/or cell-bound IgE in a patient. To begin, donor basophils and associated leukocytes are obtained from one or more donors. More particularly, blood is drawn from one or more donors, and basophils and associated leukocytes are then extracted therefrom using known procedures.

Next, the donor basophils and associated leukocytes are challenged (contacted) with control serum. As used herein, the term "control serum" refers to serum that is collected from a donor who (i) has previously tested negative for CU and/or (ii) does not exhibit clinical symptoms of CU. Prior to challenging the donor basophils and associated leukocytes with control serum, the donor basophils and associated leukocytes may first be primed with interleukin-3 (IL-3). After being challenged with control serum, the amount of histamine released by the donor basophils and associated leukocytes is quantified, preferably using a Histamine Enzyme-Linked Immunoassay (ELISA).

Next, a normalized baseline of histamine release is calculated. The normalized baseline of histamine release represents a mean percentage of histamine released by the basophils and associated leukocytes of an individual donor, plus a specified amount above such mean. For example, the invention provides that the mean percentage of histamine released by the basophils and associated leukocytes for each individual donor is calculated and, in order to derive the final normalized baseline, an amount is added to such mean. The amount added to the mean accounts for the variability in, among other things, the data that is generated using such quantitative assay to measure histamine release, such as the Histamine ELISA referenced herein. In certain preferred embodiments, the amount that is added to such mean represents a standard deviation that is derived from the data set that is used to calculate such mean. For example, the amount that is added to such mean may be 1, 2, 3, or more standard deviations of such data set. The invention provides that, in certain preferred embodiments, the amount that is added to such mean will be about 2 standard deviations.

After the normalized baseline of histamine release is calculated, a test patient's serum may be reacted (i.e., contacted) with the donor basophils and associated leukocytes. Next, the percentage of histamine released by the donor basophils and associated leukocytes in response to the test patient serum is quantitatively measured, such as by using a Histamine ELISA. The percentage of histamine released by the donor basophils and associated leukocytes in response to the patient serum is then compared to the normalized baseline of histamine release.

The invention provides that the percentage of histamine released by the donor basophils and associated leukocytes in response to the patient (test) serum is compared to the normalized baseline of histamine release using a CU Index, which itself represents another embodiment of the present invention. More particularly, the CU Index is calculated using the following formula:

$$(\alpha/\beta) \times 10 = \text{CU Index}$$

The $\alpha$ unit represents the amount (percentage) of histamine released by the donor basophils and associated leukocytes in response to the patient serum. The $\beta$ unit represents the normalized baseline of histamine release, which is calculated as described above.

According to such embodiments of the invention, a CU Index of 10 or more indicates that the donor basophils and associated leukocytes were stimulated by the patient serum. In such embodiments, a CU Index of 10 or more is further indicative that the patient tests positive for auto-immune CU. More particularly, a CU Index of 10 or more is indicative that the patient harbors auto-antibodies against IgE, FcεRI, FcεRI (CD23), other basophil proteins, and/or combinations thereof. Of course, the 10-multiplier in the formula referenced above, for calculating the CU Index, is optional. For example, in the event that the 10 multiplier is not used, a CU Index of 1 or more would indicate that, e.g., the donor basophils and associated leukocytes were stimulated by the test patient serum.

The invention further provides that the CU Index is proportional to the amount of histamine released by the donor basophils and associated leukocytes in response to the patient serum. Accordingly, the CU Index may also be used as an indicator of the severity of the patient's auto-immune CU. That is, the CU Index may not only be used as a metric to diagnose a patient as having auto-immune CU, it is further useful for providing information regarding the severity of a patient's auto-immune CU. Such information will be useful to a treating physician in determining how to prevent, treat and/or manage a patient's auto-immune CU. For example, the type (and dosage) of pharmaceutical that is administered to the patient, if any, may be influenced by the patient's CU Index, i.e., the severity of the auto-immune CU.

Furthermore, the CU Index may be used as a metric to determine whether a patient should be treated with an immune modulating drug. For example, if a patient exhibits a CU Index of 10 or more (using the formula of $(\alpha/\beta) \times 10 = \text{CU}$ Index, referenced above), a physician may determine that such patient should be treated with one or more immune modulating drugs. Furthermore, just as the CU Index will serve as an indicator of the severity of a patient's auto-immune CU, the CU Index will further indicate how efficacious an immune modulating drug may be upon administration to a patient. The invention further provides that the compositions and methods described herein may be used to determine whether an individual should be included in a clinical trial for immune modulating drugs (or other agents) that are being tested for auto-immune diseases, such as auto-immune CU. For example, in the case of a candidate immune modulating drug, patients having a CU Index of 10 or more will preferably be included in the trial (whereas patients having a CU Index of 10 or less will preferably be excluded from the trial).

Still further, the invention provides that the methods described herein are further useful for (i) preparing donor basophils and associated leukocytes for use in diagnosing auto-immune chronic urticaria and (ii) detecting and measuring auto-antibodies to cell-surface IgE receptors or cell-bound IgE in a patient, as described above.

According to additional embodiments of the present invention, kits are provided which contain donor basophils and associated leukocytes for use in diagnosing auto-immune chronic urticaria. Such kits preferably include instructions or other information, which convey the normalized baseline of histamine release for the applicable donor basophils and associated leukocytes (and, furthermore, instructions, forms, and/or programs for calculating a CU Index for a test patient). Such kits, which comprise donor basophils and associated leukocytes (having a known and indicated normalized baseline of histamine release) may be used to test the serum of a plurality of patients to (i) calculate each patient's CU Index and (ii) diagnose each patient has auto-immune CU positive or negative (and, if positive, the severity of such patient's auto-immune CU).

The following examples are provided to further illustrate the methods and compositions of the present invention. These examples are illustrative only and are not intended to limit the scope of the invention in any way.

EXAMPLES

Patient Serum Collection. A minimum volume of 1.0 mL of serum should be obtained from each patient. The blood from which the serum is to be prepared should be allowed to clot prior to centrifugation according to standard clinical laboratory practices for routine serological testing. The serum sample(s) may be shipped at ambient temperature, provided that if there is a delay in shipment, the sample must be frozen at −20° C. and shipped on ice packs. Hemolyzed serum samples may produce errant results and, as such, should be avoided to the extent possible.

Assay Procedure. The chart below indicates an approximate number of donor tubes of whole blood to draw, depending on the number of patients to be tested for auto-immune CU using the methods described herein.

| Patient Samples | Sodium Heparin Donor Tubes Collected (9 mL) |
| --- | --- |
| 1-19 | 1 |
| 20-48 | 2 |
| 49-77 | 3 |
| 78-106 | 4 |

The required number of stimulation buffer vials, containing IL-3, should be thawed to room temperature, along with 1 vial of anti-IgE antibodies (e.g., Anti-IgE, 0.2 mg, Beckman Coulter, Catalog Number IM0277, reconstituted with 2 mL of LAL apyrogenic water). The stimulation buffer used in this example is offered by ALPCO, Catalog Number 02-B-Cast-STB. A 1:25 dilution of anti-IgE is prepared by mixing 13 µL of 0.1 mg/mL stock with 312 µL PBS (Phosphate Buffered Saline—azide free).

Donor heparinized blood is first centrifuged at 200×g for 10 minutes at 22° C. The top plasma layer is removed and dispensed into an approved biohazard disposal container and 1.4 mL of concentrated blood containing both the basophil containing fraction (BCF) and red blood cells (RBCs) are transferred into a sterile tube. The blood concentrate containing the BCF is then mixed by gentle vortexing, and then centrifuged at 500×g for 10 minutes at 22° C. The plasma layer is once again removed and dispensed into an approved biohazard disposal container. Care should be taken so as not to disturb the BCF that is located at the interface of the plasma and red blood cell (RBC) fractions. The remaining cell preparation, containing BCF and RBCs, is gently vortexed.

The volume of stimulation buffer listed in the table found in FIG. 1 is then added to the cell preparation (containing the BCF and RBC) and mixed by gentle vortexing; this forms the "cell suspension" (as shown in FIG. 1). Next, 75 µL of the cell suspension, followed by 75 µL of stimulation buffer, stimulation control buffer, total histamine solution, anti-IgE antibodies, negative control serum, positive control serum, and/or test patient serum, are dispensed into 1.7 mL tubes, as described in the table below.

| Tube (See Key Below) | 1 | 2 | 3 | 4 | 5 | 6 | 7 | 8 | 9 | 10 | 11-N |
|---|---|---|---|---|---|---|---|---|---|---|---|
| Stimulation Buffer (µL) | 75 | 75 | 75 | 75 | | | | | | | |
| Stimulation Control (µL) | | | | | 75 | 75 | | | | | |
| Patient/Control serum (µL) | | | | | | | 75 | 75 | 75 | 75 | 75 |

Key:
Tubes 1 and 2: Total Histamine
Tubes 3 and 4: Stimulation buffer
Tubes 5 and 6: Anti-IgE
Tube 7: Negative Patient Control
Tube 8: Positive Patient Control
Tube 9: Negative Control (Serum 1)
Tube 10: Negative Control (Serum 2)
Tube 11-N: Test Patient Serum The tubes are then gently vortexed, while being shielded from light, for 30 (+/−2) minutes at 37° C. in a water bath. Next, 75 µL of cold blocking buffer, e.g., a sterile solution containing phosphate buffered saline and one percent bovine serum albumin, are added to each tube, which is then gently vortexed. The covered tubes are then placed in an ice water bath for 5 minutes. All tubes, except Tubes 1 and 2 above, are subsequently centrifuged at 500×g for 5 minutes. Without extracting any (or a significant number of) red blood cells, 100 µL of supernatant is carefully removed and placed into each of two microtiter plate wells (e.g., Costar 3790 Round Bottom Microtiter Plates, Fisher Cat #07-200-94). If a supernatant is contaminated with a sufficient number of red blood cells, the supernatant should be returned to the reaction tube, mixed, and re-centrifuged. The supernatants are stored at −70±10° C. until tested using the Histamine ELISA protocol.

In addition, 100 µL of blocking buffer are added to Tubes 1 and 2, which are then (a) placed in a dry ice ethanol bath for 1.5 minutes and (b) removed and placed in a 37° C. bath for 3.5 minutes. The foregoing steps (a) and (b) are repeated two more times. 140 µL of supernatant (the cells should be substantially lysed) are then transferred to each of two clean microtiter plate wells (or Bioblock tubes). These samples represent the total histamine contained in the cell preparation and are used to calculate the percent of histamine released. These supernatants are also stored at −70±10° C. until tested using the Histamine ELISA protocol described below.

The soluble histamine concentration (ng/mL) in the collected supernatants is then determined using a Histamine ELISA protocol. Such Histamine ELISAs are commercially-available and may be obtained, for example, from Beckman Coulter, e.g., Beckman Coulter Catalog No. IM2015 96t. Prior to ELISA analysis, the anti-IgE and total histamine samples are diluted 1:10 and the positive serum and negative serum samples are diluted 1:2. The buffer samples and patient serum samples are not diluted. A non-limiting example of an ELISA test format is illustrated in the table below.

| Description | Donor Cells | Challenge Solution |
|---|---|---|
| Total Histamine (Duplicate) | 75 µL | 75 µL Stimulation Buffer |
| Negative Control (Duplicate) | 75 µL | 75 µL Stimulation Buffer |
| Positive Control (Duplicate) | 75 µL | 75 µL Anti-IgE in LAL/PBS |
| Positive Serum | 75 µL | 75 µL positive control serum |
| Negative Serum | 75 µL | 75 µL negative control serum |
| Patient Serum | 75 µL | 75 µL undiluted patient serum |

Next, the concentration of histamine (ng/mL) measured by the Histamine ELISA is multiplied by the dilution factor, if any, and final volume to derive the total amount (ng) of histamine. The percentage of histamine release for negative control, positive control, and test patient serum samples are then calculated. More particularly, for undiluted samples (e.g., buffer samples), the results may be used directly from the Histamine ELISA. For diluted samples, e.g., anti-IgE, total histamine, positive/negative control serum samples, etc., the concentration of histamine (ng/mL) is multiplied by the dilution factor. For the total histamine samples, the concentration of histamine (ng/mL) is further multiplied by 0.325 mL to determine the total (ng) amount of Histamine released. For anti-IgE, buffer, and all serum samples, the concentration of histamine (ng/mL) is further multiplied by 0.225 mL to determine the total (ng) amount of Histamine released.

Next, the percentage of histamine released is calculated. In order to calculate the percentage of histamine released in the anti-IgE, buffer, and serum samples, the total (ng) amount of histamine released in the anti-IgE, buffer, and serum samples is divided by the total (ng) amount of histamine released in the total histamine samples. This quotient is then multiplied by 100 to derive the percentage of histamine released. Such calculation is further shown below:

$$(\Delta/\Omega) \times 100 = \% \text{ Histamine Released, wherein}$$

$\Delta$ represents the total (ng) amount of histamine released in the anti-IgE, buffer, or serum samples (as the case may be); and $\Omega$ represents the total (ng) amount of histamine released in the total histamine samples.

Next, the CU Index is calculated. More particularly, as described above, the CU

Index is calculated using the following formula:

$$(\alpha/\beta) \times 10 = \text{CU Index.}$$

The $\alpha$ unit represents the amount (percentage) of histamine released by the donor basophils and associated leukocytes in response to the patient serum. In this case, the donor basophils and associated leukocytes having been derived from individuals who, for example, do not exhibit clinical signs of CU, whereas the "patient serum" is derived from an individual who is being tested for auto-immune CU. The β unit represents the normalized baseline of histamine release, which is the mean percentage of histamine released by the donor basophils and associated leukocytes, plus a specified amount above such mean (such as two standard deviations of the data generated for the donor basophils and associated leukocytes).

Example Calculations. For purposes of further illustration, the following provides an exemplary set of data and certain calculations derived therefrom, as described above.

| Tube Number | Histamine (ng/mL)[1] | Histamine (ng) | Mean Total Histamine[2] | % Histamine Release[3] | CU Index[4] |
|---|---|---|---|---|---|
| 1-Histamine | 29.86*0.325 mL | 9.70 | 10.09 | 96.1 | |
| 2-Histamine | 32.24*0.325 mL | 10.48 | | 103.9 | |
| 3-Buffer | 0.54*0.225 mL | 0.12 | | 1.2 | 0.8 |
| 4-Anti-IgE | 30.7*0.225 mL | 6.91 | | 68.5 | 46.6 |
| 5-Patient A | 2.35*0.225 mL | 0.53 | | 5.3 | 3.6 |
| 6-Patient B | 10.03*0.225 mL | 2.26 | | 22.4 | 15.2 |

1. Derived from ELISA results.
2. Average of Tube #1 and #2 Histamine (ng).
3. Histamine (ng)/Mean Total Histamine × 100.
4. CU Index is based on a donor having a normalized baseline of histamine release of 14.7.

In the exemplary data summarized in the table above, Patient A would be considered to have tested negative for auto-immune CU, insofar as his/her CU Index score is less than 10. In contrast, Patient B would be considered to have tested positive for auto-immune CU, insofar as his/her CU Index score is greater than 10.

The following tables provide yet further sets of exemplary data and the calculations described above, including the calculation of the normalized baseline of histamine for three separate donors of basophils and associated leukocytes (below).

| Control Serum ID | Donor A | | Donor B | | Donor C | |
|---|---|---|---|---|---|---|
| 1 | | 9.3 | 6.7 | 2.6 | 4.3 | 4.9 | 3.8 |
| 2 | 3.0 | 6.8 | 4.2 | 2.5 | 4.1 | 3.7 | 3.8 |
| 3 | | | 2.1 | 2.3 | 4.9 | 1.9 | 2.7 |
| 4 | 4.4 | 8.4 | 4.1 | 7.2 | 5.0 | 1.6 | 4.3 |
| 5 | | 8.7 | 2.9 | 2.9 | 2.1 | 1.7 | 2.5 |
| 6 | | 10.4 | 4.6 | 5.2 | 6.7 | 1.3 | 13.3 |
| 7 | | 3.5 | 1.8 | 2.5 | 3.2 | 2.2 | 2.5 |
| 8 | | 8.0 | 2.1 | 1.8 | 2.9 | 5.2 | 5.9 |
| 9 | | 1.2 | 2.6 | 2.1 | 1.9 | 3.3 | 2.6 |
| 10 | 3.4 | 15.0 | 2.7 | 8.4 | 7.6 | 7.6 | 9.1 |
| 11 | | 6.7 | 3.1 | 3.5 | | | |
| 12 | | 13.2 | 2.3 | 2.2 | 2.1 | | |
| 13 | | 0.9 | | 5.8 | 6.0 | | |
| 14 | | 6.5 | | | | | |
| 15 | | 3.9 | | | | | |
| 16 | | 4.9 | | | | | |
| 17 | | 7.3 | | | | | |
| Mean | | 5.3 | | 4.0 | | 4.2 | |
| Std. Dev. | 3.5 | 2.0 | 3.0 | | | | |
| Mean + 2 Std. Dev. | 12.3 | 8.0 | 10.2 | | | | |

Preferably, as in the data summarized in the table above, a minimum of 20 values are obtained from at least two Histamine ELISAs. In the table above, the normalized baseline of histamine release for Donors A, B, and C of 12.3, 8.0, and 10.2, respectively, represents the mean percentage of histamine released by the donor basophils and associated leukocytes, plus two standard deviations. The table below summarizes the calculation of the CU Index values for several patients, based on the normalized baseline of histamine release for Donor B above.

| Patient ID | % Histamine Release | CU Index Calculation | CU Index |
|---|---|---|---|
| A1 | 9.9 | = (9.9/8)*10 | 12.4 |
| B1 | 8.8 | = (8.8/8)*10 | 11.0 |
| C1 | 34.8 | = (34.8/8)*10 | 43.6 |

-continued

| Patient ID | % Histamine Release | CU Index Calculation | CU Index |
|---|---|---|---|
| D1 | 7 | = (7/8)*10 | 8.8 |
| E1 | 6.9 | = (6.9/8)*10 | 8.6 |
| F1 | 6.4 | = (6.4/8)*10 | 7.9 |
| G1 | 9 | = (9/8)*10 | 11.3 |
| H1 | 11.1 | = (11.1/8)*10 | 13.9 |
| I1 | 28.5 | = (28.5/8)*10 | 35.6 |

Based on the foregoing CU Index for each patient, the following table summarizes the diagnosis for each patient. Specifically, the following table indicates whether each patient has tested positive or negative for auto-immune CU (i.e., whether the CU Index for each such patient is more than 10).

| Patient ID | CU Index | Auto-Immune CU |
|---|---|---|
| A1 | 12.4 | Positive |
| B1 | 11.0 | Positive |
| C1 | 43.6 | Positive |
| D1 | 8.8 | Negative |
| E1 | 8.6 | Negative |
| F1 | 7.9 | Negative |
| G1 | 11.3 | Positive |
| H1 | 13.9 | Positive |
| I1 | 35.6 | Positive |

Furthermore, based on the foregoing CU Index for each patient, it may be determined that—among the patients testing positive for auto-immune CU—patient C1's and patient I1's auto-immune CU is more severe than that of any of patients A1, B1, and G1.

While there have been shown and described fundamental features of the invention as applied to preferred embodiments thereof, it will be understood that various omissions and substitutions and changes in the form and details of the methods and compositions illustrated and/or described herein, and in their operation, may be made by those of ordinary skill in the art without departing from the spirit of the invention. For example, it is expressly intended that all combinations of those elements and/or method steps which perform substantially the same function in substantially the same way to achieve the same results are within the scope of the invention.

What is claimed is:

1. A method for diagnosing auto-immune chronic urticaria in a patient, the method comprising:
    reacting a serum sample from the patient with donor basophils and associated leukocytes obtained from an individual donor;
    measuring histamine released by the donor basophils and associated leukocytes in response to the patient serum; and
    using the measured histamine released to calculate a CU index score, wherein the CU index is represented by the following formula:

$(\alpha/\beta)$=CU Index, wherein $\alpha$ is the amount of histamine released by the donor basophils and associated leukocytes in response to the patient serum, and $\beta$ is a normalized baseline of histamine release, wherein the normalized baseline of histamine release is a mean percentage plus 1 or more standard deviations thereof of histamine released by the donor basophils and associated leukocytes following challenges with control sera obtained from serum donors that do not exhibit clinical symptoms of chronic urticaria;
    wherein the CU index score is an indicator of a diagnosis of auto-immune chronic urticaria in the patient.

2. The method of claim 1, wherein the diagnosis is positive for autoimmune chronic urticaria when the CU index score is 1 or more.

3. The method of claim 1, wherein the CU index multiplied by 10 to provide the CU index score.

4. The method of claim 3, wherein the diagnosis is positive for autoimmune chronic urticaria when the CU index score is 10 or more.

5. The method of claim 1, wherein said measuring is by histamine Enzyme-Linked Immunoassay (ELISA).

6. The method of claim 3, wherein said measuring is by Histamine Enzyme-Linked Immunoassay (ELISA).

7. The method of claim 1, wherein a CU index score of 1 or more indicates that the patient should be treated with an immune modulating drug.

8. The method of claim 3, wherein a CU index score of 10 or more indicates that the patient should be treated with an immune modulating drug.

9. The method of claim 1, wherein the normalized baseline of histamine release is a mean percentage plus 2 or more standard deviations of histamine released by donor basophils and associated leukocytes of an individual donor following challenge with a control serum obtained from one or more donors that do not exhibit clinical symptoms of chronic urticaria.

10. The method of claim 1, wherein the normalized baseline of histamine release is a mean percentage plus about 2 standard deviations of histamine released by donor basophils and associated leukocytes of an individual donor following challenge with a control serum obtained from one or more donors that do not exhibit clinical symptoms of chronic urticaria.

11. A method for monitoring efficacy of an immune modulating drug in treatment of auto- immune chronic urticaria in a patient to whom the drug was administered, the method comprising:
    reacting a serum sample from the patient with donor basophils and associated leukocytes obtained from an individual donor;
    measuring histamine released by the donor basophils and associated leukocytes in response to the patient serum; and
    using the measured histamine released to calculate a CU index score, wherein the CU index is represented by the following formula:

$(\alpha/\beta)$=CU Index, wherein $\alpha$ is the amount of histamine released by the donor basophils and associated leukocytes in response to the patient serum, and $\beta$ is a normalized baseline of histamine release, wherein the normalized baseline of histamine release is a mean percentage plus 1 or more standard deviations thereof of histamine released by the donor basophils and associated leukocytes following challenges with control sera obtained from serum donors that do not exhibit clinical symptoms of chronic urticaria;
    wherein the CU index score is an indicator of efficacy of the immune modulating drug in the patient.

12. The method of claim 11, wherein the CU index multiplied by 10 to provide the CU index score.

13. The method of claim 11, wherein the normalized baseline of histamine release is a mean percentage plus 2 or more standard deviations of histamine released by donor basophils and associated leukocytes of an individual donor following challenge with a control serum obtained from one or more donors that do not exhibit clinical symptoms of chronic urticaria.

14. The method of claim 11, wherein the normalized baseline of histamine release is a mean percentage plus about 2 standard deviations of histamine released by donor basophils and associated leukocytes of an individual donor following challenge with a control serum obtained from one or more donors that do not exhibit clinical symptoms of chronic urticaria.

15. The method of claim 11, wherein said measuring is by histamine Enzyme-Linked Immunoassay (ELISA).

16. The method of claim 12, wherein said measuring is by histamine Enzyme-Linked Immunoassay (ELISA).

17. A method for determining whether a subject should be included in a clinical trial of a candidate drug for treatment of chronic urticaria, the method comprising:
    reacting a serum sample from the patient with donor basophils and associated leukocytes obtained from an individual donor;
    measuring histamine released by the donor basophils and associated leukocytes in response to the patient serum; and
    using the measured histamine released to calculate a CU index score, wherein the CU index is represented by the following formula:

$(\alpha/\beta)$=CU Index, wherein $\alpha$ is the amount of histamine released by the donor basophils and associated leukocytes in response to the patient serum, and $\beta$ is a normalized baseline of histamine release, wherein the normalized baseline of histamine release is a mean percentage plus 1 or more standard deviations thereof of histamine released by the donor basophils and associated leukocytes following challenges with control sera obtained from serum donors that do not exhibit clinical symptoms of chronic urticaria;

wherein the CU index score is an indicator of efficacy of the immune modulating drug in the patient.

18. The method of claim 17, wherein the CU index multiplied by 10 to provide the CU index score.

19. The method of claim 17, wherein the normalized baseline of histamine release is a mean percentage plus 2 or more standard deviations of histamine released by donor basophils and associated leukocytes of an individual donor following challenge with a control serum obtained from one or more donors that do not exhibit clinical symptoms of chronic urticaria.

20. The method of claim 17, wherein the normalized baseline of histamine release is a mean percentage plus about 2 standard deviations of histamine released by donor basophils and associated leukocytes of an individual donor following challenge with a control serum obtained from one or more donors that do not exhibit clinical symptoms of chronic urticaria.

21. The method of claim 17, wherein said measuring is by histamine Enzyme-Linked Immunoassay (ELISA).

22. The method of claim 18, wherein said measuring is by histamine Enzyme-Linked Immunoassay (ELISA).

* * * * *